United States Patent
Baker, Jr. et al.

(10) Patent No.: US 8,229,530 B2
(45) Date of Patent: Jul. 24, 2012

(54) SYSTEM AND METHOD FOR DETECTION OF VENOUS PULSATION

(75) Inventors: Clark R. Baker, Jr., Castro Valley, CA (US); Paul Mannheimer, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1537 days.

(21) Appl. No.: 11/716,263

(22) Filed: Mar. 9, 2007

(65) Prior Publication Data

US 2008/0221417 A1    Sep. 11, 2008

(51) Int. Cl.
   *A61B 5/1455*    (2006.01)
(52) U.S. Cl. .................. 600/324; 600/323
(58) Field of Classification Search .......... 600/322–324, 600/331, 336, 310, 340
   See application file for complete search history.

(56) References Cited

U.S. PATENT DOCUMENTS

| | | | |
|---|---|---|---|
| 4,380,439 A | 4/1983 | Kreitenberg | |
| 4,759,369 A | 7/1988 | Taylor | |
| 4,824,242 A | 4/1989 | Frick et al. | |
| 4,854,699 A | 8/1989 | Edgar, Jr. | |
| 4,859,057 A | 8/1989 | Taylor et al. | |
| 4,863,265 A | 9/1989 | Flower et al. | |
| 4,867,557 A | 9/1989 | Takatani et al. | |
| 4,907,594 A | 3/1990 | Muz | |
| 4,911,167 A | 3/1990 | Corenman et al. | |
| 4,926,867 A | 5/1990 | Kanda et al. | |
| 4,955,379 A | 9/1990 | Hall | |
| 4,960,126 A | 10/1990 | Conlon et al. | |
| 4,968,137 A | 11/1990 | Yount | |
| 5,025,791 A | 6/1991 | Niwa | |
| 5,058,588 A | 10/1991 | Kaestle | |
| 5,218,962 A * | 6/1993 | Mannheimer et al. | 600/331 |
| 5,251,632 A | 10/1993 | Delpy | |
| 5,263,244 A | 11/1993 | Centa et al. | |
| 5,267,562 A | 12/1993 | Ukawa et al. | |
| 5,267,563 A | 12/1993 | Swedlow et al. | |
| 5,278,627 A | 1/1994 | Aoyagi et al. | |
| 5,285,783 A | 2/1994 | Secker | |
| 5,297,548 A | 3/1994 | Pologe | |
| 5,299,120 A | 3/1994 | Kaestle | |

(Continued)

FOREIGN PATENT DOCUMENTS

WO    WO03/063697 A1    8/2003

OTHER PUBLICATIONS

ISR/PCTUS2008/003179; Dated of mailing: Jun. 30, 2008.

(Continued)

*Primary Examiner* — Eric Winakur
*Assistant Examiner* — Chu Chuan (JJ) Liu (57) ABSTRACT

In accordance with an embodiment of the present technique, there is provided methods and systems for detecting the presence of venous pulsation by adjusting the sensitivity of a detection algorithm based on a sensor characteristic and/or notifying a caregiver of the presence of venous pulsation by ceasing display of physiological parameters. An exemplary embodiment includes receiving one or more signals from a sensor, the one or more signals corresponding to absorption of light in a patient's tissue; calculating one or more physiological parameters of the patient based on the one or more signals; displaying the patient's physiological parameters; enabling detection of venous pulsation with variable sensitivity based on a location of the sensor; and suspending or terminating the display of the one or more of the patient's physiological parameters when venous pulsation is detected.

44 Claims, 5 Drawing Sheets

U.S. PATENT DOCUMENTS

| | | |
|---|---|---|
| 5,329,922 A | 7/1994 | Atlee, III |
| 5,348,005 A | 9/1994 | Merrick et al. |
| 5,349,519 A | 9/1994 | Kaestle |
| 5,355,882 A | 10/1994 | Ukawa et al. |
| 5,390,670 A | 2/1995 | Centa et al. |
| 5,392,777 A | 2/1995 | Swedlow et al. |
| 5,396,893 A | 3/1995 | Oberg et al. |
| 5,402,777 A | 4/1995 | Warring et al. |
| 5,402,778 A | 4/1995 | Chance |
| 5,408,998 A | 4/1995 | Mersch |
| 5,417,207 A | 5/1995 | Young et al. |
| 5,458,562 A | 10/1995 | Cooper |
| 5,485,847 A | 1/1996 | Baker, Jr. |
| 5,490,505 A | 2/1996 | Diab et al. |
| 5,503,148 A | 4/1996 | Pologe et al. |
| 5,517,988 A | 5/1996 | Gerhard |
| 5,522,388 A | 6/1996 | Ishikawa et al. |
| 5,524,617 A | 6/1996 | Mannheimer |
| 5,575,285 A | 11/1996 | Takanashi et al. |
| 5,584,299 A | 12/1996 | Sakai et al. |
| 5,595,176 A | 1/1997 | Yamaura |
| 5,645,059 A | 7/1997 | Fein et al. |
| 5,662,106 A | 9/1997 | Swedlow et al. |
| 5,685,299 A | 11/1997 | Diab et al. |
| 5,690,104 A | 11/1997 | Kanemoto et al. |
| 5,715,816 A | 2/1998 | Mainiero et al. |
| 5,743,261 A | 4/1998 | Mainiero et al. |
| 5,743,263 A | 4/1998 | Baker, Jr. |
| 5,743,349 A | 4/1998 | Steinberg |
| 5,746,206 A | 5/1998 | Mannheimer |
| 5,766,127 A | 6/1998 | Pologe et al. |
| 5,810,723 A | 9/1998 | Aldrich |
| 5,817,008 A | 10/1998 | Rafert et al. |
| 5,830,137 A | 11/1998 | Scharf |
| 5,853,364 A | 12/1998 | Baker, Jr. et al. |
| 5,871,694 A | 2/1999 | Beden et al. |
| 5,891,025 A | 4/1999 | Buschmann et al. |
| 5,902,235 A | 5/1999 | Lewis et al. |
| 5,934,277 A | 8/1999 | Mortz |
| 6,018,673 A | 1/2000 | Chin et al. |
| 6,073,041 A | 6/2000 | Hu et al. |
| 6,149,597 A | 11/2000 | Kamiyama |
| 6,151,107 A | 11/2000 | Schollermann et al. |
| 6,151,516 A | 11/2000 | Kiani-Azarbayjany et al. |
| 6,151,518 A | 11/2000 | Hayashi |
| 6,178,343 B1 | 1/2001 | Bindszus et al. |
| 6,216,021 B1 | 4/2001 | Franceschini et al. |
| 6,230,035 B1 | 5/2001 | Aoyagi et al. |
| 6,258,038 B1 | 7/2001 | Haryadi et al. |
| 6,263,222 B1 | 7/2001 | Diab et al. |
| 6,272,363 B1 | 8/2001 | Casciani et al. |
| 6,278,889 B1 | 8/2001 | Robinson |
| 6,285,896 B1 | 9/2001 | Tobler et al. |
| 6,299,583 B1 | 10/2001 | Eggers et al. |
| 6,330,468 B1 | 12/2001 | Scharf |
| 6,334,065 B1 | 12/2001 | Al-Ali et al. |
| 6,339,715 B1 | 1/2002 | Bahr et al. |
| 6,374,129 B1 | 4/2002 | Chin et al. |
| 6,381,480 B1 | 4/2002 | Stoddart et al. |
| 6,385,471 B1 | 5/2002 | Mortz |
| 6,393,310 B1 | 5/2002 | Kuenstner |
| 6,393,311 B1 | 5/2002 | Edgar, Jr. et al. |
| 6,397,093 B1 | 5/2002 | Aldrich |
| 6,406,267 B1 | 6/2002 | Mondiere |
| 6,411,832 B1 | 6/2002 | Guthermann |
| 6,411,833 B1 * | 6/2002 | Baker et al. ............ 600/336 |
| 6,415,236 B2 | 7/2002 | Kobayashi et al. |
| 6,438,399 B1 | 8/2002 | Kurth |
| 6,449,501 B1 | 9/2002 | Reuss |
| 6,456,870 B1 * | 9/2002 | Rennert et al. ............ 600/310 |
| 6,461,165 B1 | 10/2002 | Takashina et al. |
| 6,480,729 B2 | 11/2002 | Stone |
| 6,494,576 B1 | 12/2002 | L'Esperance |
| 6,501,974 B2 | 12/2002 | Huiku |
| 6,519,486 B1 | 2/2003 | Edgar, Jr. et al. |
| 6,526,297 B1 | 2/2003 | Merilainen |
| 6,584,336 B1 | 6/2003 | Ali et al. |
| 6,587,704 B1 | 7/2003 | Fine et al. |
| 6,606,509 B2 | 8/2003 | Schmitt |
| 6,615,065 B1 | 9/2003 | Barrett et al. |
| 6,622,095 B2 | 9/2003 | Kobayashi et al. |
| 6,647,280 B2 | 11/2003 | Bahr et al. |
| 6,650,917 B2 | 11/2003 | Diab et al. |
| 6,671,526 B1 | 12/2003 | Aoyagi et al. |
| 6,675,031 B1 | 1/2004 | Porges et al. |
| 6,702,752 B2 | 3/2004 | Dekker |
| 6,714,803 B1 | 3/2004 | Mortz |
| 6,714,804 B2 | 3/2004 | Al-Ali et al. |
| 6,721,584 B2 * | 4/2004 | Baker et al. ............ 600/323 |
| 6,754,515 B1 | 6/2004 | Pologe |
| 6,770,028 B1 | 8/2004 | Ali et al. |
| 6,780,158 B2 | 8/2004 | Yarita |
| 6,801,799 B2 | 10/2004 | Mendelson |
| 6,810,277 B2 | 10/2004 | Edgar, Jr. et al. |
| 6,819,950 B2 | 11/2004 | Mills |
| 6,839,585 B2 | 1/2005 | Lowery et al. |
| 6,842,635 B1 | 1/2005 | Parker |
| 6,845,256 B2 | 1/2005 | Chin et al. |
| 6,859,658 B1 | 2/2005 | Krug |
| 6,879,850 B2 | 4/2005 | Kimball |
| 6,898,452 B2 | 5/2005 | Al-Ali et al. |
| 6,947,780 B2 | 9/2005 | Scharf |
| 6,947,781 B2 | 9/2005 | Asada et al. |
| 6,970,792 B1 | 11/2005 | Diab |
| 6,987,994 B1 | 1/2006 | Mortz |
| 7,039,538 B2 | 5/2006 | Baker, Jr. |
| 7,194,293 B2 | 3/2007 | Baker, Jr. |
| 7,209,774 B2 | 4/2007 | Baker, Jr. |
| 7,457,652 B2 | 11/2008 | Porges et al. |
| 2004/0230107 A1 | 11/2004 | Asada et al. |
| 2004/0236196 A1 | 11/2004 | Diab et al. |
| 2005/0197552 A1 | 9/2005 | Baker, Jr. |
| 2005/0197579 A1 | 9/2005 | Baker, Jr. |
| 2005/0256386 A1 | 11/2005 | Chan et al. |
| 2006/0030764 A1 | 2/2006 | Porges et al. |
| 2006/0200015 A1 | 9/2006 | Baker, Jr. |
| 2006/0224053 A1 | 10/2006 | Black et al. |
| 2006/0253007 A1 | 11/2006 | Cheng et al. |
| 2007/0077200 A1 | 4/2007 | Baker, Jr. |
| 2007/0100220 A1 | 5/2007 | Baker, Jr. |
| 2007/0208242 A1 | 9/2007 | Baker, Jr. |
| 2008/0077022 A1 | 3/2008 | Baker, Jr. |
| 2008/0221462 A1 | 9/2008 | Baker, Jr. |
| 2008/0221463 A1 | 9/2008 | Baker, Jr. |

OTHER PUBLICATIONS

U.S. Appl. No. 11/528,295, filed Sep. 27, 2006, Baker, Jr.

* cited by examiner

SYSTEM AND METHOD FOR DETECTION OF VENOUS PULSATION

BACKGROUND OF THE INVENTION

1. Field of the Invention

The present invention relates to pulse oximetry and, more particularly, to processing signals from a sensor.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Sensors exist that are designed to be applied to foreheads, digits, or various other locations on a patient's body. A phenomenon called "venous pulsation" may typically occur at sensor sites where the vasculature lacks venous valves, such as the head, but venous pulsation may also occur at less typical sites as well. Venous pulsation refers to a pulse generated from the return flow of venous blood to the heart. Because the hemoglobin in venous blood has already delivered oxygen to tissue, sensor readings based on venous pulsation may result in artificially low calculations of blood oxygen saturation (denoted as $SpO_2$ when calculated from a pulsatile measurement). In addition, due to prominent harmonics in a venous pressure wave, pulse rate calculations based on incorrect sensor readings may be double or triple the patient's actual pulse rate. Unlike motion artifacts that may be intermittent, occurring only when a patient moves, venous pulsation can continue uninterrupted for hours. Thus, whereas inaccurate readings due to patient movement or other intermittent noise may disappear relatively quickly, inaccurate reading due to venous pulsation may last for a long time.

In some circumstances, venous pulsation may also occur at the extremities, such as fingers and feet. For example, when a patient is in an odd position, such as when a patient's extremities are placed lower than his heart for an extended period of time, venous pulsation may develop. In addition, patients with respiratory problems or patients undergoing surgery may exhibit venous pulsation even in the extremities. For example, during surgery, a patient may experience venous pulsation at a digit due to partial occlusions from a blood pressure cuff.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a method for detecting venous pulsation, including receiving one or more signals from a sensor, the signals corresponding to absorption of light in a patient's tissue; determining a characteristic of the sensor; performing a venous pulsation detection algorithm on the one or more signals, wherein the venous pulsation detection algorithm is performed at a sensitivity level based on the characteristic of the sensor; and determining whether venous pulsation is present based on the performance of the venous pulsation detection algorithm.

There is further provided a method for preventing display of inaccurate measurements in the presence of venous pulsation, including receiving one or more signals from a sensor, the one or more signals corresponding to absorption of light in a patient's tissue; calculating one or more physiological parameters of the patient based on the one or more signals; determining if venous pulsation is present based on the one or more signals; and suspending or terminating a display of the one or more of the patient's physiological parameters based on detection of venous pulsation.

There is further provided a method for detecting venous pulsation, including receiving a signal from a sensor indicating sensor type; enabling or disabling detection of venous pulsation based on the sensor type; and calculating one or more physiological parameters based on one or more received signals corresponding to absorption of light in a patient's tissue.

There is further provided a method for detecting venous pulsation, including receiving one or more signals from a sensor, the one or more signals corresponding to absorption of light in a patient's tissue; calculating one or more physiological parameters of the patient based on the one or more signals; displaying the patient's physiological parameters; enabling detection of venous pulsation with variable sensitivity based on a location of the sensor; and suspending or terminating the display of the one or more of the patient's physiological parameters when venous pulsation is detected.

There is further provided a system for detecting venous pulsation, including means for receiving one or more signals from a sensor, the signals corresponding to absorption of light in a patient's tissue; means for determining a characteristic of the sensor; means for performing a venous pulsation detection algorithm on the one or more signals, wherein the venous pulsation detection algorithm is performed at a sensitivity level based on the characteristic of the sensor; and means for determining whether venous pulsation is present based on the performance of the venous pulsation detection algorithm.

There is further provided a system for preventing display of inaccurate measurements in the presence of venous pulsation, including means for receiving one or more signals from a sensor, the one or more signals corresponding to absorption of light in a patient's tissue; means for calculating one or more physiological parameters of the patient based on the one or more signals; means for determining if venous pulsation is present based on the one or more signals; and means for suspending or terminating a display of the one or more of the patient's physiological parameters based on detection of venous pulsation.

There is further provided a system for detecting venous pulsation, including means for receiving one or more signals from a sensor, the one or more signals corresponding to absorption of light in a patient's tissue; means for calculating one or more physiological parameters of the patient based on the one or more signals; means for displaying the patient's physiological parameters; means for enabling detection of venous pulsation with variable sensitivity based on a location of the sensor; and means for suspending or terminating the display of the one or more of the patient's physiological parameters when venous pulsation is detected.

There is further provided a system for detecting venous pulsation, including means for receiving a signal from a sensor indicating sensor type; means for enabling or disabling detection of venous pulsation based on the sensor type; and means for calculating one or more physiological parameters based on one or more received signals corresponding to absorption of light in a patient's tissue.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention are directed to preventing the display of possibly inaccurate physiological parameters in the presence of venous pulsation, detecting the presence of venous pulsation by enabling or disabling venous pulsation detection based on the type of sensor used, and/or adjusting the sensitivity of a detection algorithm based on a sensor characteristic (e.g., actual location or intended location of the sensor). The actual or intended location of the sensor may be determined by user input, a location detection algorithm, and/or a signal from the sensor. Based on the sensor location, a pulse oximeter may adjust the sensitivity of its venous pulsation detection algorithm. For example, a more sensitive venous pulsation detection algorithm may be used when the sensor is in a location where venous pulsation is likely to occur, such as the forehead. When the sensor is located where venous pulsation is less likely to occur, for example, on a digit, a less sensitive venous pulsation algorithm may be utilized, or detection of venous pulsation may be disabled. In addition, when venous pulsation is detected, display of some or all of the patient's physiological parameters may be suspended or terminated.

Accordingly, sensors may be provided with identification information, such as the sensor name, or a bit which indicates where the sensor is designed to be placed. This information can be read by the pulse oximeter, and the sensitivity of algorithms for detecting venous pulsation may be adjusted as a result. In addition, the appropriate algorithms and/or calibration coefficients for calculating physiological parameters may be selected based on the identification information. When venous pulsation is detected using such algorithms and/or coefficients, the pulse oximeter may cease the display of $SpO_2$ and/or pulse rate to avoid conveying inaccurate data.

Figure 1:
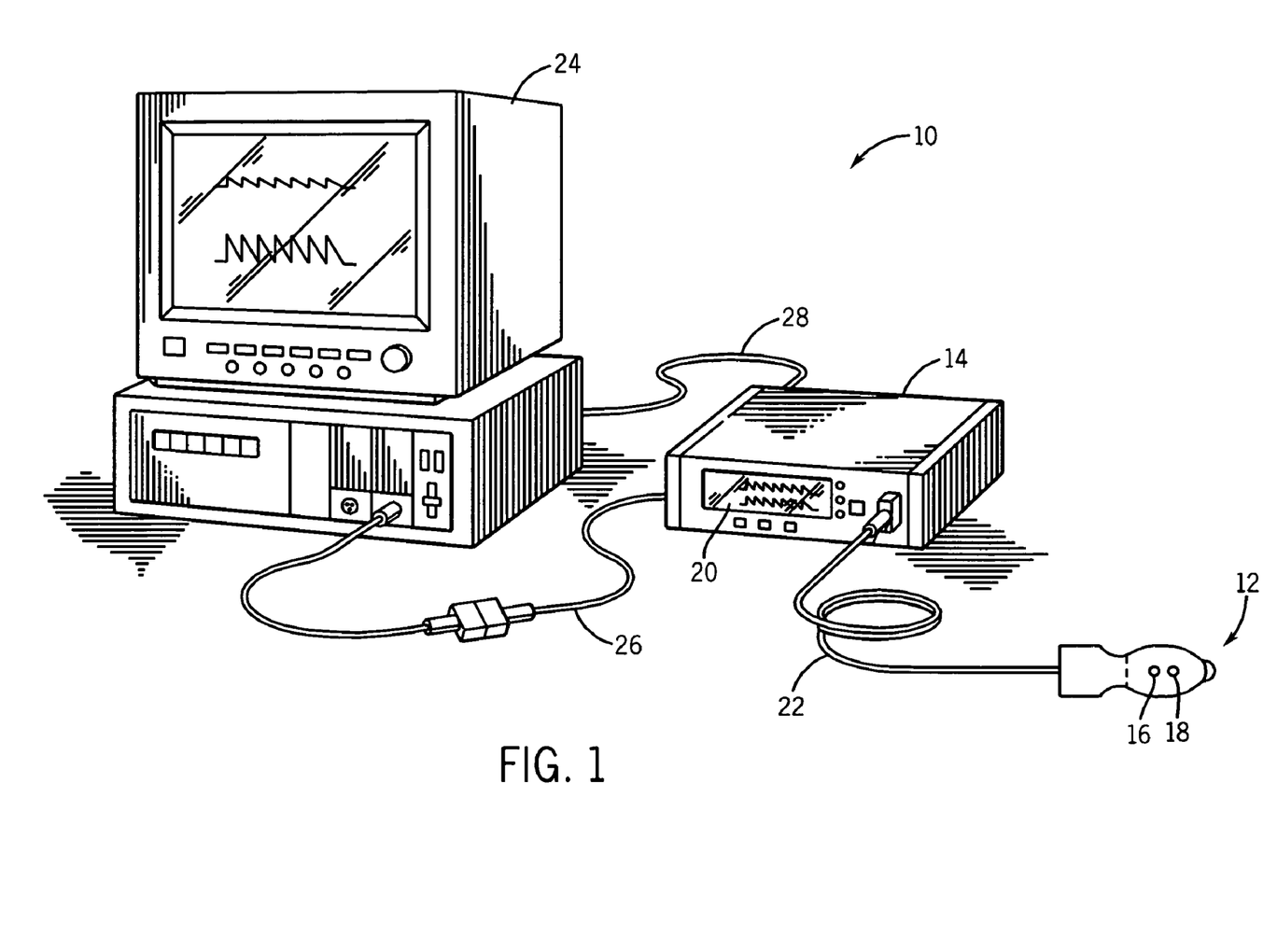
FIG. 1 is a perspective view of a pulse oximeter coupled to a multi-parameter patient monitor and a sensor in accordance with an exemplary embodiment of the present invention.

FIG. 1 is a perspective view of a pulse oximetry system 10 in accordance with an exemplary embodiment of the present invention. The system 10 may include a sensor 12 and a pulse oximetry monitor 14. The sensor 12 may include an emitter 16 for emitting light at certain wavelengths into a patient's tissue and a detector 18 for detecting the light after it is reflected and/or absorbed by the patient's tissue. The monitor 14 may be configured to calculate physiological parameters and to display the physiological parameters and/or other information about the system on a display 20. Further, the monitor 14 may be configured to suspend or terminate display of some or all of the physiological parameters when venous pulsation is detected, as described below. The sensor 12 may be communicatively coupled to the monitor 14 via a cable 22 or other suitable device, such as, for example, a wireless transmission device (not shown).

The pulse oximetry system 10 may also include a multi-parameter patient monitor 24. The multi-parameter patient monitor 24 may be included in the system 10 to provide a central display for information from the monitor 14 and from other medical monitoring devices or systems (not shown). For example, the multi-parameter patient monitor 24 may display a patient's $SpO_2$ and pulse rate information from the monitor 14 and blood pressure from a blood pressure monitor (not shown). In addition to the monitor 14, or alternatively, the multi-parameter patient monitor 24 may be configured to calculate physiological parameters. The monitor 14 may be communicatively coupled to the multi-parameter patient monitor 24 via a cable 26 or 28 coupled to a sensor input port or a digital communications port, respectively.

Figure 2:
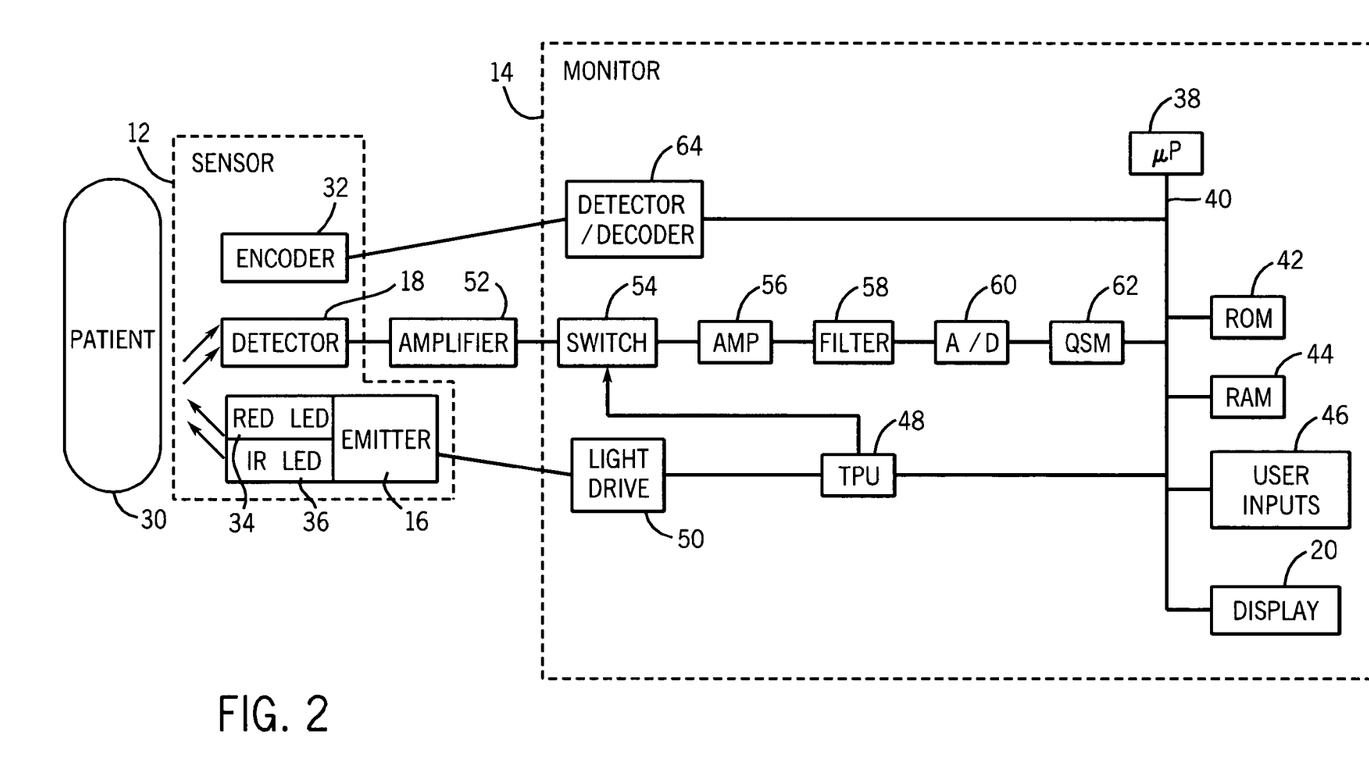
FIG. 2 is a block diagram of the pulse oximeter and sensor coupled to a patient in accordance with an exemplary embodiment of the present invention.

FIG. 2 is a block diagram of the exemplary pulse oximetry system 10 of FIG. 1 coupled to a patient 30 in accordance with present embodiments. Specifically, certain components of the sensor 12 and the monitor 14 are illustrated in FIG. 2. The sensor 12 includes the emitter 16, the detector 18, and an encoder 32. It should be noted that the emitter 16 is configured to emit at least two wavelengths of light, e.g., RED and IR, into a patient's tissue 30. Hence, the emitter 16 may include a RED LED 34 and an IR LED 36 for emitting light into the patient's tissue 30 at the wavelengths used to calculate the patient's physiological parameters. In certain embodiments, the RED wavelength may be between about 600 nm and about 700 nm, and the IR wavelength may be between about 800 nm and about 1000 nm. Alternative light sources may be used in other embodiments of the present invention. For example, a single wide-spectrum light source may be used, and the detector 18 may be configured to detect light only at certain wavelengths. In another example, the detector 18 may detect a wide spectrum of wavelengths of light, and the monitor 14 may process only those wavelengths which are of interest. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present techniques.

In one embodiment, the detector 18 may be configured to detect the intensity of light at the RED and IR wavelengths. In operation, light enters the detector 18 after passing through the patient's tissue 30. The detector 18 converts the intensity of the received light into an electrical signal. The light intensity is directly related to the absorbance and/or reflectance of light in the tissue 30. That is, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 30. The calculation of $SpO_2$ from measured RED and IR absorption values is described, for example, in U.S. Pat. No. 5,853,364, issued Dec. 29, 1998, entitled "METHOD AND APPARATUS FOR ESTIMATING PHYSIOLOGICAL PARAMETERS USING MODEL-BASED ADAPTIVE FILTERING" by Clark R. Baker, Jr. and Thomas J. Yorkey, which is herein incorporated by reference in its entirety for all purposes.

The encoder 32 may contain information about the sensor 12, such as what type of sensor it is (e.g., whether the sensor is intended for placement on a forehead or digit) and the wavelengths of light emitted by the emitter 16. This information may allow the monitor 14 to select appropriate algorithms and/or calibration coefficients for calculating the patient's physiological parameters. For example, the information may indicate whether venous pulsation detection should be enabled, or provide a level of sensitivity that should be utilized in a venous pulsation detection algorithm. The encoder 32 may, for instance, be a coded resistor which stores values corresponding to the type of the sensor 12 and to the wavelengths of light emitted by the emitter 16. These coded values may be communicated to the monitor 14, which utilizes a look-up table to determine which algorithms and/or calibration coefficients correspond to the coded values. In another embodiment, the encoder 32 may be a memory on which the type of the sensor 12, the wavelengths of light emitted by the emitter 16, the proper calibration coefficients, and/or the algorithms to be used for calculating physiological parameters may be stored for communication to the monitor 14.

As set forth above, in accordance with present embodiments, information received from the sensor 12 (e.g., sensor characteristics) may indicate whether venous pulsation detection should be enabled or disabled, or what level of sensitivity should be utilized in a venous pulsation detection algorithm. For example, if the information received from the sensor 12 indicates that it is located on a patient's forehead, the monitor 14 may enable venous pulsation detection and/or increase a sensitivity level of a venous pulsation detection algorithm because venous pulsation is likely to occur at that location. In another example, if the information received from the sensor 12 indicates that it is located on a patient's digit, the monitor 14 may disable venous pulsation detection or reduce the sensitivity of a venous pulsation detection algorithm because venous pulsation is not likely to occur at that location. The sensitivity level of a venous pulsation detection algorithm may be adjusted by utilizing different equations, calibration coefficients, and/or criteria when measuring venous pulsation. For example, increasing sensitivity may be achieved by reducing a time threshold for which venous pulsations must be observed before being addressed.

Signals from the detector 18 and the encoder 32 may be transmitted to the monitor 14. The monitor 14 generally includes a microprocessor 38 connected to an internal bus 40. Also connected to the bus are a read-only memory (ROM) 42, a random access memory (RAM) 44, user inputs 46, and the display 20. A time processing unit (TPU) 48 provides timing control signals to a light drive circuitry 50 which controls when the emitter 16 is illuminated and the multiplexed timing for the RED LED 34 and the IR LED 36. The TPU 48 also controls the gating-in of signals from detector 18 through an amplifier 52 and a switching circuit 54. These signals are sampled at the proper time, depending upon which light source is illuminated. The received signal from the detector 18 may be passed through an amplifier 56, a low pass filter 58, and an analog-to-digital converter 60. The digital data may then be stored in a queued serial module (QSM) 62 for later downloading to the RAM 44 as the QSM 62 fills up. In one embodiment, there may be multiple separate parallel paths having the amplifier 56, the filter 58, and the A/D converter 60 for multiple light wavelengths or spectra received.

The microprocessor 38 may determine whether venous pulsation is present and calculate $SpO_2$ using various algorithms based on the value of the received signals corresponding to the light received by the detector 18. These algorithms use calibration coefficients and thresholds which may be empirically determined, corresponding to, for example, the likelihood of venous pulsation at a sensor site and the wavelengths of light used. Furthermore, as set forth above, the sensitivity to detecting venous pulsation may be affected by the algorithm, the calibration coefficients, and/or the criteria (e.g., thresholds) utilized.

Signals corresponding to information about the sensor 12 may be transmitted from the encoder 32 to a decoder 64. These signals may, for example, include information about the type of the sensor 12 used, such as whether the sensor 12 is a forehead or digit sensor. In addition, the signals may correspond to the wavelengths of light emitted by the emitter 16, and/or other sensor characteristics. The decoder 64 translates these signals and determines the algorithms and/or calibration coefficients to use for calculating physiological parameters, as described below. These algorithms and calibration coefficients may be stored in ROM 42. In addition, the encoder 32 may contain the algorithms and/or calibration coefficients for use with the sensor 12. The user inputs 46 may also be used to enter information about the sensor, such as the sensor location and/or the wavelengths of light emitted by emitter 16.

After the proper calculation information has been selected, the microprocessor 38 determines whether venous pulsation is present and calculates the patient's physiological parameters. Exemplary algorithms for detecting venous pulsation are described in U.S. patent application Ser. No. 10/796,584, filed Mar. 8, 2004, entitled "METHOD AND APPARATUS FOR OPTICAL DETECTION OF MIXED VENOUS AND ARTERIAL BLOOD PULSATION IN TISSUE" by Clark R. Baker, Jr.; U.S. patent application Ser. No. 11/528,295, filed Sep. 27, 2006, entitled "METHOD AND APPARATUS FOR DETECTION OF VENOUS PULSATION" by Clark R. Baker, Jr.; and U.S. patent application Ser. No. 11/716,132, filed concurrently herewith, entitled "SYSTEM AND METHOD FOR VENOUS PULSATION DETECTION USING NEAR INFRARED WAVELENGTHS" by Clark R. Baker, Jr., all of which are herein incorporated by reference in their entirety for all purposes. The calculated physiological parameters may then be displayed on the display 20. If venous pulsation is detected, a notification of venous pulsation may be displayed on the display 20 and/or an audible alarm may sound. Additionally, display of at least one of the physiological parameters may be suspended or terminated since it is deemed to be inaccurate.

Cease Display of Physiological Parameters

Figure 3:
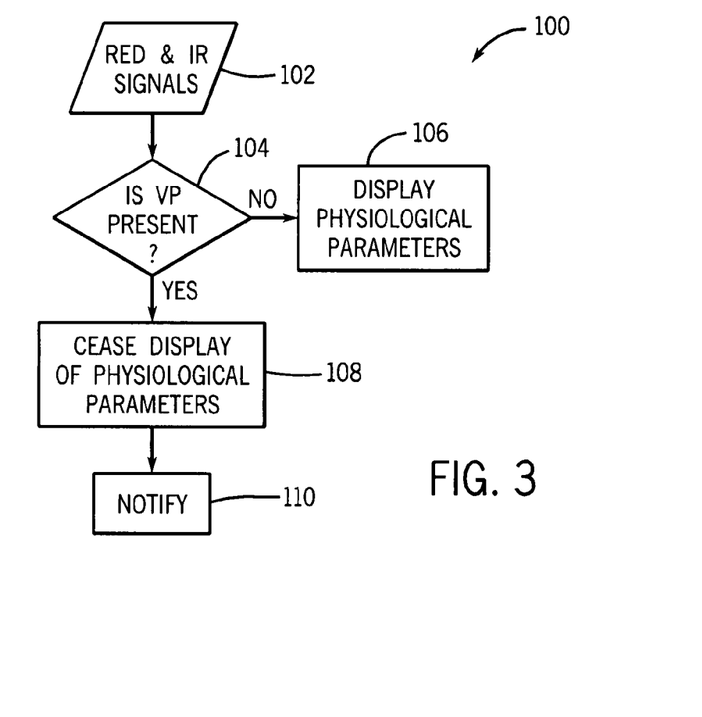
FIG. 3 is a flow chart of a process related to preventing the display of inaccurate measurements in the presence of venous pulsation in accordance with an exemplary embodiment of the present invention.

In addition to notifying a caregiver of the presence of venous pulsation when detected, a monitor 14 may cease display of one or more calculated physiological parameters since the calculations may be inaccurate. FIG. 3 illustrates a general process 100 for ceasing display of physiological parameters. In one embodiment, signals corresponding to detected RED and IR light 102 may be received from the sensor 12. Based on the signals 102, the process 100 determines if venous pulsation is present (Block 104). If venous pulsation is not present, physiological parameters may be calculated and displayed, for example, on the display 20 (Block 106).

However, if venous pulsation is present, display of some or all of the patient's physiological parameters may be suspended or terminated (Block 108). That is, the monitor 14 may cease display of pulse rate and/or SpO$_2$. This may prevent the caregiver from receiving erroneous readings due to the interference of venous pulsation with the physiological parameter calculations. In one embodiment, cessation may be a suspension, and display of the physiological data may be reinitiated when venous pulsation is no longer detected. In another embodiment, cessation may be a termination, and a caregiver may be required to reset the monitor 14 before physiological data can be displayed again. In addition, the monitor 14 may be configured to cease display of physiological parameters only when venous pulsation has been detected for at least a certain period of time. The period of time may be any desired threshold, such as, for example, 20 seconds, 40 seconds, or 60 seconds, and may be a preset value or a user-input value. The monitor 14 may also be configured to notify the caregiver of the presence of venous pulsation by emitting an auditory alert and/or displaying a visual alert, such as on the display 20 (Block 110). Accordingly, if venous pulsation is detected, for example, for at least 20 seconds, display of SpO$_2$ may be terminated, and a visual alert on the display 20 may notify the caregiver that venous pulsation has been detected. In another example, if venous pulsation is detected for at least 40 seconds, display of both pulse rate and SpO$_2$ may be suspended until venous pulsation is no longer detected, and an audible alert may notify the caregiver that venous pulsation has been detected.

Figure 4:
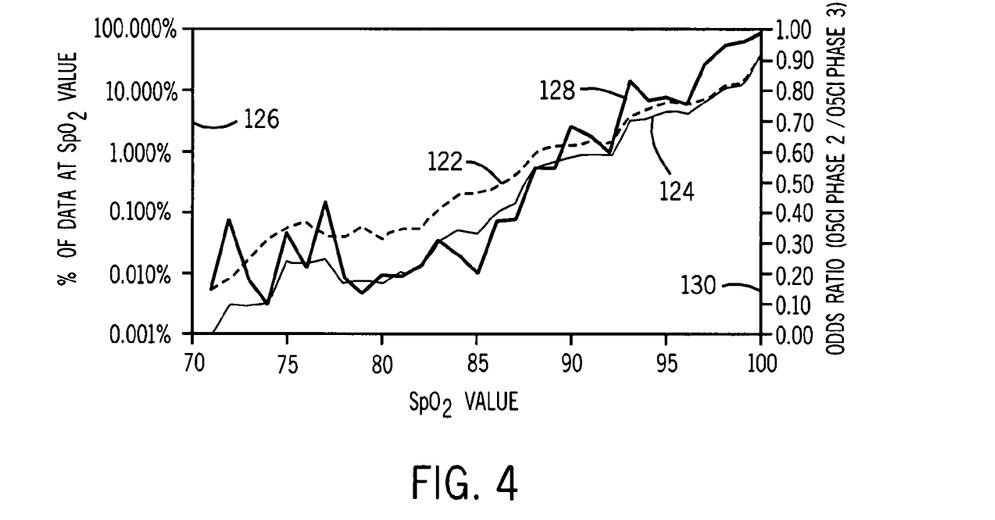
FIG. 4 is a graph of the distribution of $SpO_2$ in patients as calculated by an oximeter in accordance with an exemplary embodiment of the present invention.

Embodiments of the present invention were implemented along with existing techniques in data from surgical trials to demonstrate relative benefits. Forty-three patients were monitored during surgeries in which venous pulsation was likely to occur. FIG. 4 illustrates a graph 120 of calculated SpO$_2$ values for the patients. Pulse oximetry sensors were placed on the patients' foreheads. During surgery, the patients were continuously monitored by an anesthesiologist, mechanically ventilated, and typically received high concentrations of inspired oxygen. Under these circumstances, SpO$_2$ values that are not in the high 90s are likely due to venous pulsation. A dashed line 122 shows the distribution of reported SpO$_2$ values where SpO$_2$ was calculated in the same manner regardless of whether venous pulsation was detected. A solid line 124 shows the distribution of reported SpO$_2$ values where SpO$_2$ updates were immediately suspended upon detection of venous pulsation, and SpO$_2$ display was interrupted when venous pulsation had been detected for at least 40 seconds. The lines 122 and 124 are histograms plotted on a logarithmic scale 126. A line with circles 128, corresponding to an axis 130, shows an odds ratio of displaying each possible SpO$_2$ value with and without an enhancement for venous pulsation detection. That is, line 128 illustrates the ratio of the odds of each SpO$_2$ value being calculated with venous pulsation disabled versus with venous pulsation enabled. It is apparent from the graph 120 that suspension of SpO$_2$ calculation and subsequent interruption of SpO$_2$ display during periods of venous pulsation achieved a threefold reduction in the incidence of reported SpO$_2$ values below 85%, which low values are presumably due to venous pulsation. In other words, embodiments of the present invention substantially reduce the number of reported SpO$_2$ values that were inaccurate due to venous pulsations.

Enable Venous Pulsation Detection Based on Sensor Type

Figure 5:
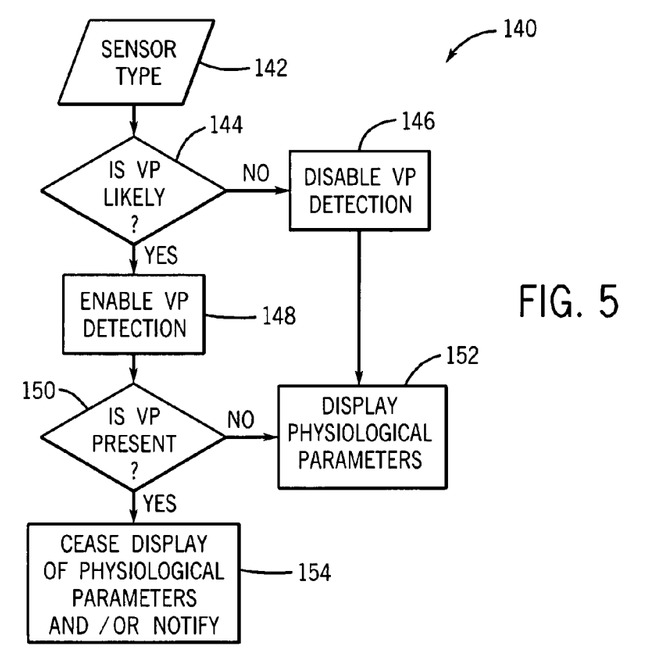
FIG. 5 is a flow chart of a process related to enabling venous pulsation detection when certain types of sensors are used in accordance with an exemplary embodiment of the present invention.
Figures 6, 7:
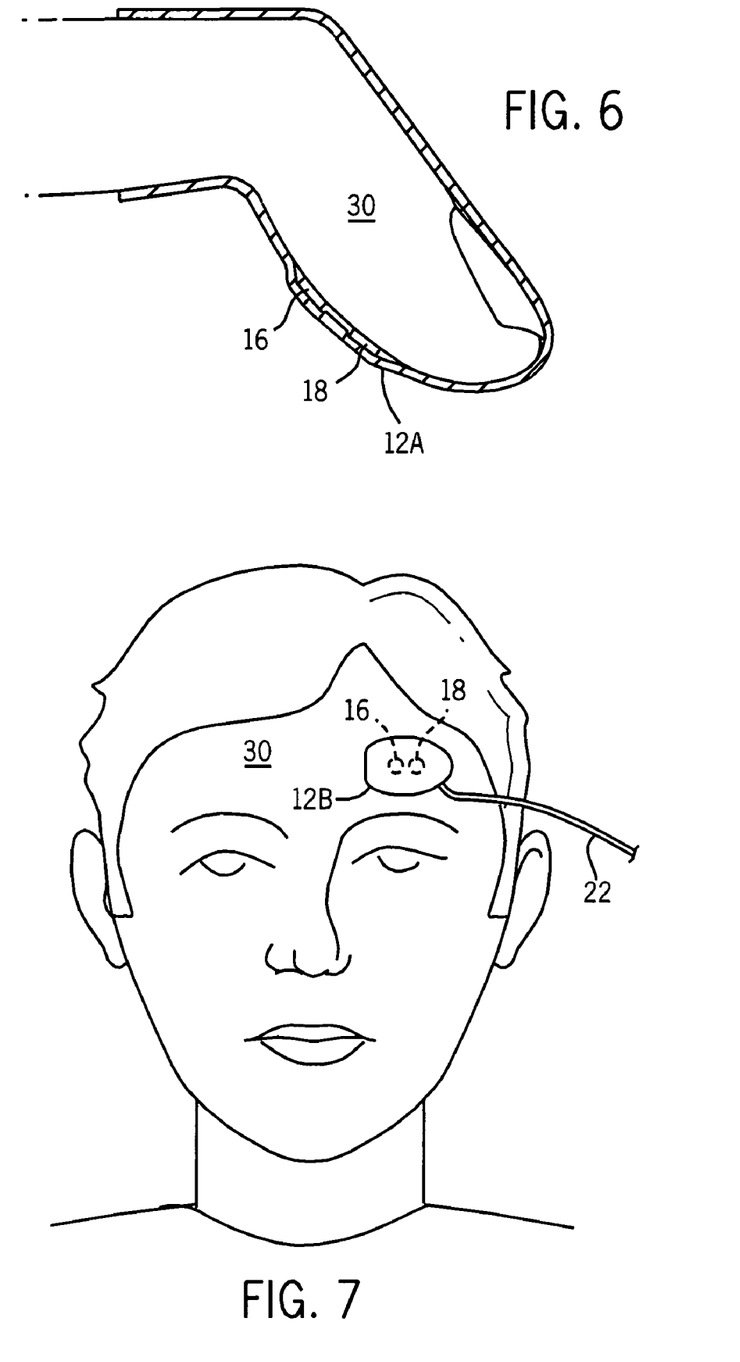
FIG. 6 illustrates a digit sensor in accordance with an exemplary embodiment of the present invention.
FIG. 7 illustrates a forehead sensor in accordance with an exemplary embodiment of the present invention.

In another embodiment, illustrated as a general process 140 in FIG. 5, venous pulsation detection may be enabled based on a signal from the sensor 12 indicating what type of sensor it is. For example, the sensor 12 may be placed on a patient's extremity or forehead. FIG. 6 illustrates a digit sensor 12A abutting the tissue 30 of a patient's finger. The emitter 16 may emit two or more wavelengths of light into the tissue 30. This light is then scattered and reflected back to the detector 18. Signals representative of the detected light are then transmitted to the monitor 14. In addition, the encoder 32 may transmit a signal to the monitor 14 indicating that the sensor 12A is designed for placement on a digit. In a different sensor design, a forehead sensor 12B is illustrated abutting the tissue 30 of a patient's forehead in FIG. 7. In this embodiment, the encoder 32 may transmit a signal to the monitor 14 indicating that the sensor 12B is designed for placement on the forehead.

Returning to FIG. 5, based on a sensor type 142 (e.g., forehead or digit), detection of venous pulsation may be enabled or disabled, as described in the process 140. The sensor type 142 may be transmitted from the sensor 12 to the monitor 14. The sensor 12 may transmit this information via the encoder 32. Based on the sensor type 142, the process 140 determines whether the sensor 12 is located at a site where venous pulsation is likely to occur (Block 144).

If the sensor 12 is designed for use on a site where venous pulsation is not likely to occur, such as a digit, venous pulsation detection may be disabled (Block 146). However, if the sensor 12 is designed for use on a site where venous pulsation is likely to occur, such as the forehead, venous pulsation detection may be enabled (Block 148).

If detection of venous pulsation is enabled, a determination is made as to whether venous pulsation is present (Block 150). If venous pulsation is not detected, or if detection of venous pulsation is not enabled, one or more physiological parameters may be calculated and displayed, for example, on the display 20 (Block 152). If venous pulsation is present, display of some or all of the patient's physiological parameters may be ceased and/or the caregiver may be notified of the presence of venous pulsation, for example, via an auditory or visual alarm (Block 154).

Figure 8:
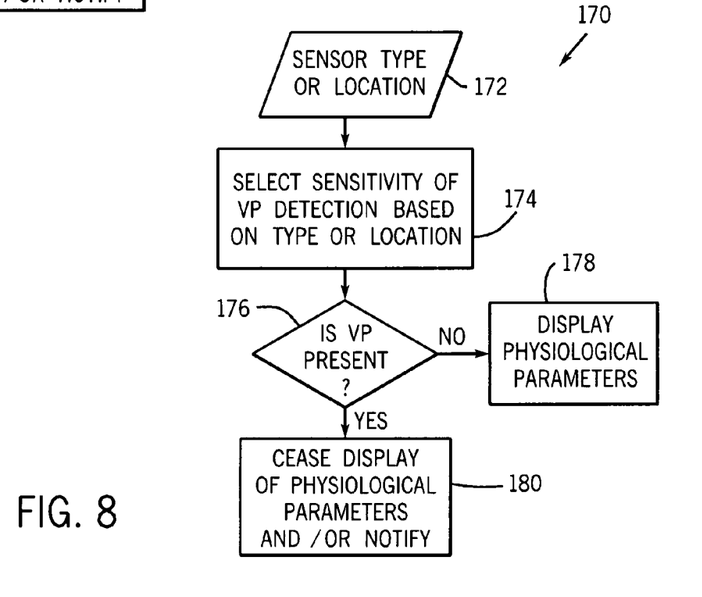
FIG. 8 is a flow chart of a process related to selecting a sensitivity level for a venous pulsation detection algorithm in accordance with an exemplary embodiment of the present invention.

Select Sensitivity of Venous Pulsation Detection Based on Sensor Type or Location A general process 170 for enabling varying levels of venous pulsation detection sensitivity is illustrated in FIG. 8. The sensor type of location 172 may be provided or determined. For example, sensor information may be transmitted from a memory on the sensor 12 and may include data relating to the type of sensor being utilized (e.g., digit or forehead). The sensor location may also be determined by user input or by a process such as that described in U.S. patent application Ser. No. 11/716,437, filed concurrently herewith, entitled "DETECTION OF OXIMETRY SENSOR SITES BASED ON WAVEFORM CHARACTERISTICS" by Clark R. Baker, Jr., which is herein incorporated by reference in its entirety for all purposes.

Based on the sensor type or location 172, a sensitivity level for a venous pulsation detection algorithm may be selected (Block 174). The sensitivity of the venous pulsation detection algorithm may be adjusted, for example, by using a variable threshold for a venous pulsation detection metric, or requiring an indication of venous pulsation for a variable time period (e.g., 20-40 seconds) before determining that venous pulsation is present. For example, if the sensor type or location 172 indicates that the sensor is located or is designed to be placed at a site where venous pulsation is likely to be present, such as the forehead, algorithms, calibration coefficients, and/or criteria may be used which are designed to detect even small signs of venous pulsation or to give more weight to data indicative of venous pulsation. However, if the sensor type or location 172 indicates that the sensor is located or is designed to be placed at a site where venous pulsation is not likely to be present, such as a digit, a less sensitive venous pulsation detection algorithm may be utilized. Selecting the sensitivity of the venous pulsation algorithm may include selecting one detection algorithm utilizing different calibration coefficients and/or criteria. For example, the less sensitive venous pulsation detection algorithm may require that venous pulsation be indicated for a longer period of time before it is determined that venous pulsation is present. In one embodiment, selecting the sensitivity may include selecting different algorithms.

The process 170 then determines if venous pulsation is present (Block 176). If venous pulsation is not detected, one or more physiological parameters may be calculated and displayed, for example, on the display 20 (Block 178). If venous pulsation is present, display of some or all of the patient's physiological parameters may be ceased and/or the caregiver may be notified of the presence of venous pulsation, for example, via an auditory or visual alarm (Block 180).

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized in conjunction with the measurement and/or analysis of carboxyhemoglobin, methemoglobin, total hemoglobin, intravascular dyes, and/or water content. Likewise, the technique may be employed using other techniques for measuring pulse shape, different sequences of filtering, different constants, and so forth. The invention is to cover all modifications, equivalents, and alternatives falling within the spirit and scope of the invention as defined by the following appended claims.

What is claimed is:

1. A method for detecting venous pulsation, comprising:
    receiving one or more signals from a sensor, the signals corresponding to absorption of light in a patient's tissue;
    determining a characteristic of the sensor;
    performing a venous pulsation detection algorithm on the one or more signals, wherein the venous pulsation detection algorithm is performed at a sensitivity level based on the characteristic of the sensor; and
    determining whether venous pulsation is present based on the performance of the venous pulsation detection algorithm.

2. The method of claim 1, wherein determining the characteristic comprises determining an intended location of the sensor from an encoder in the sensor.

3. The method of claim 1, wherein determining the characteristic comprises determining a location of the sensor from a user input.

4. The method of claim 1, wherein determining the characteristic comprises determining a likely location of the sensor from a sensor location detection algorithm.

5. The method of claim 1, wherein determining the characteristic comprises determining whether the sensor is located or intended to be located on a digit or forehead.

6. The method of claim 1, wherein the sensitivity level of the venous pulsation detection algorithm is greater when the sensor is located at a site where venous pulsation is likely to occur than when the sensor is located at a site where venous pulsation is not likely to occur.

7. The method of claim 6, wherein the sensitivity level of the venous pulsation detection algorithm is greater when the sensor is located on a forehead of the patient.

8. The method of claim 1, comprising calculating one or more physiological parameters based on the one or more signals corresponding to absorption of light in the patient's tissue.

9. The method of claim 8, comprising ceasing a display of values of the one or more physiological parameters when a criterion relating to detected venous pulsation is met.

10. The method of claim 8, wherein the one or more physiological parameters comprise blood oxygen saturation, pulse rate, or a combination thereof.

11. The method of claim 1, comprising providing an auditory or visual alarm when venous pulsation is detected.

12. The method of claim 1, wherein the sensitivity level of the venous pulsation detection algorithm is determined by selecting the venous pulsation detection algorithm from among a plurality of venous pulsation detection algorithms with different sensitivities.

13. A method for preventing display of inaccurate measurements in the presence of venous pulsation, comprising:
   receiving one or more signals from a sensor, the one or more signals corresponding to absorption of light in a patient's tissue;
   determining a characteristic of the sensor;
   calculating one or more physiological parameters of the patient based on the one or more signals;
   determining if venous pulsation is present based on the one or more signals, wherein determining if venous pulsation is present comprises performing a venous pulsation detection algorithm at a sensitivity level based on the characteristic of the sensor; and
   suspending or terminating a display of the one or more of the patient's physiological parameters based on detection of venous pulsation.

14. The method of claim 13, wherein suspending the display of the one or more of the patient's physiological parameters comprises ceasing the display until venous pulsation is undetected for a period of time.

15. The method of claim 13, wherein terminating the display of the one or more of the patient's physiological parameters comprises ceasing the display until a reset is activated.

16. The method of claim 13, comprising suspending or terminating the display of the one or more of the patient's physiological parameters when venous pulsation is detected for at least a time equal to a time threshold.

17. The method of claim 16, wherein the time threshold is about 40 seconds.

18. The method of claim 13, wherein the one or more physiological parameters comprise blood oxygen saturation, pulse rate, or a combination thereof.

19. The method of claim 13, comprising providing a notification of the presence of venous pulsation.

20. The method of claim 19, wherein the notification comprises an auditory or visual alarm.

21. A method, comprising:
   receiving a signal from a sensor indicating sensor type;
   enabling or disabling a function configured to detect venous pulsation based on the sensor type and determining whether the venous pulsation is present when the function is enabled; and
   subsequent to enabling or disabling the function, calculating one or more physiological parameters based on one or more received signals corresponding to absorption of light in a patient's tissue.

22. The method of claim 21, wherein the function configured to detect venous pulsation is enabled when the location of the sensor is at a site where venous pulsation is likely to occur and is disabled when the location of the sensor is at a site where venous pulsation is not likely to occur.

23. The method of claim 22, wherein the site where venous pulsation is likely to occur is a forehead of the patient and the site where venous pulsation is not likely to occur is a digit of the patient.

24. The method of claim 21, comprising ceasing a display of values of the one or more physiological parameters when a criterion relating to detected venous pulsation is met.

25. The method of claim 21, providing an auditory or visual alarm when venous pulsation is detected.

26. A method for detecting venous pulsation, comprising:
   receiving one or more signals from a sensor, the one or more signals corresponding to absorption of light in a patient's tissue;
   calculating one or more physiological parameters of the patient based on the one or more signals;
   displaying the patient's physiological parameters;
   enabling a function configured to detect venous pulsation with variable sensitivity based on a location of the sensor and determining whether the venous pulsation is present when the function is enabled; and
   suspending or terminating the display of the one or more of the patient's physiological parameters when venous pulsation is detected.

27. The method of claim 26, wherein the one or more physiological parameters comprise blood oxygen saturation, pulse rate, or a combination thereof.

28. The method of claim 26, comprising suspending or terminating the display of the one or more of the patient's physiological parameters when venous pulsation is detected for at least a time threshold.

29. The method of claim 28, wherein the time threshold is about 40 seconds.

30. The method of claim 26, comprising determining the location of the sensor from an encoder in the sensor, a user input, a sensor location detection algorithm, or a combination thereof.

31. The method of claim 26, wherein the function configured to detect venous pulsation is more sensitive when the sensor is located at a site where venous pulsation is likely to occur than when the sensor is located at a site where venous pulsation is not likely to occur.

32. The method of claim 31, wherein the site where venous pulsation is likely to occur is a forehead of the patient and the site where venous pulsation is not likely to occur is a digit of the patient.

33. The method of claim 26, providing an auditory or visual alarm when venous pulsation is detected.

34. The method of claim 26, wherein the variable sensitivity is greater when the sensor is located on a forehead than when the sensor is located on a digit.

35. A system for detecting venous pulsation, comprising:
   means for receiving one or more signals from a sensor, the signals corresponding to absorption of light in a patient's tissue;
   means for determining a characteristic of the sensor;
   means for performing a venous pulsation detection algorithm on the one or more signals, wherein the venous pulsation detection algorithm is performed at a sensitivity level based on the characteristic of the sensor; and
   means for determining whether venous pulsation is present based on the performance of the venous pulsation detection algorithm.

36. The system of claim 35, comprising means for providing an auditory or visual alarm when venous pulsation is detected.

37. The system of claim 35, wherein the sensitivity level of the venous pulsation detection algorithm is greater when the sensor is located on a forehead than when the sensor is located on a digit.

38. A system for preventing display of inaccurate measurements in the presence of venous pulsation, comprising:
   means for receiving one or more signals from a sensor, the one or more signals corresponding to absorption of light in a patient's tissue;
   means for determining a characteristic of the sensor;
   means for calculating one or more physiological parameters of the patient based on the one or more signals;
   means for performing a venous pulsation detection algorithm on the one or more signals, wherein the venous pulsation detection algorithm is configured to perform at a sensitivity level based on the characteristic of the sensor;

means for determining if venous pulsation is present based on the one or more signals; and means for suspending or terminating a display of the one or more of the patient's physiological parameters based on detection of venous pulsation.

39. The system of claim 38, comprising means for providing an auditory or visual alarm when venous pulsation is detected.

40. A system for detecting venous pulsation, comprising:

means for receiving one or more signals from a sensor, the one or more signals corresponding to absorption of light in a patient's tissue;

means for calculating one or more physiological parameters of the patient based on the one or more signals;

means for displaying the patient's physiological parameters;

means for enabling a function for detection of venous pulsation with variable sensitivity based on a location of the sensor and determining whether the venous pulsation is present when the function is enabled; and means for suspending or terminating the display of the one or more of the patient's physiological parameters when venous pulsation is detected.

41. The system of claim 40, comprising means for providing an auditory or visual alarm when venous pulsation is detected.

42. The system of claim 40, wherein the variable sensitivity is greater when the sensor is located on a forehead than when the sensor is located on a digit.

43. A system, comprising:

means for receiving a signal from a sensor indicating sensor type;

means for enabling or disabling a function for detection of venous pulsation based on the sensor type and determining whether the venous pulsation is present when the function is enabled; and means for calculating one or more physiological parameters, subsequent to enabling or disabling the function, based on one or more received signals corresponding to absorption of light in a patient's tissue.

44. The system of claim 43, comprising means for providing an auditory or visual alarm when venous pulsation is detected.

* * * * *